United States Patent [19]
Burdeska et al.

[11] Patent Number: 5,142,059
[45] Date of Patent: Aug. 25, 1992

[54] MONOSULFONATED 2-(2'-HYDROXYPHENYL)-BENZOTRIAZOLES

[75] Inventors: Kurt Burdeska, Basel; Gerhard Reinert, Allschwil, both of Switzerland

[73] Assignee: Ciba-Geigy Corporation, Ardsley, N.Y.

[21] Appl. No.: 579,421

[22] Filed: Sep. 7, 1990

[30] Foreign Application Priority Data

Sep. 11, 1989 [CH] Switzerland .......... 3290/89

[51] Int. Cl.$^5$ .......... C07D 249/20
[52] U.S. Cl. .......... 548/260
[58] Field of Search .......... 548/260

[56] References Cited

U.S. PATENT DOCUMENTS

| | | | |
|---|---|---|---|
| 4,226,763 | 10/1980 | Dexter | 260/45.8 |
| 4,275,004 | 6/1981 | Winter | 260/206 |
| 4,278,589 | 7/1981 | Dexter | 260/45.8 |
| 4,315,848 | 2/1982 | Dexter | 260/45.8 |
| 4,347,180 | 8/1982 | Winter | 260/206 |
| 4,990,623 | 2/1991 | Berenbaum et al. | 548/260 |

FOREIGN PATENT DOCUMENTS 0006564 1/1980 European Pat. Off. .
8800942 2/1988 World Int. Prop. O. .

*Primary Examiner*—Patricia L. Morris
*Attorney, Agent, or Firm*—Marla J. Mathias; George R. Dohmann

[57] ABSTRACT

Monosulfonated 2-(2'-hydroxyphenyl)-benzotriazoles of the formula

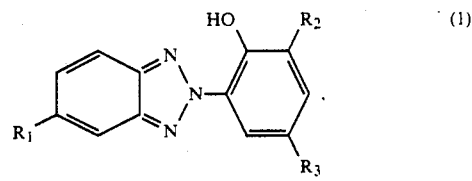

in which $R_1$ is hydrogen or chlorine and one of $R_2$ and $R_3$ is chlorine or lower alkyl and the other is a radical of the formula

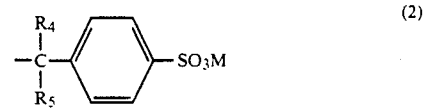

in which $R_4$ and $R_5$ independently of one another are hydrogen or methyl and M is hydrogen, an alkali metal or ammonium.

The compounds of the formula (1) are used as UV absorbers for polyamide fibres, wool and mixtures thereof.

5 Claims, No Drawings

MONOSULFONATED 2-(2'-HYDROXYPHENYL)-BENZOTRIAZOLES

The present invention relates to monosulfonated 2-(2'-hydroxyphenyl)-benzotriazoles, to a process for their preparation and to their use as UV absorbers for polyamide fibres, wool and mixtures thereof.

The monosulfonated 2-(2'-hydroxyphenyl)-benzotriazoles according to the invention have the general formula

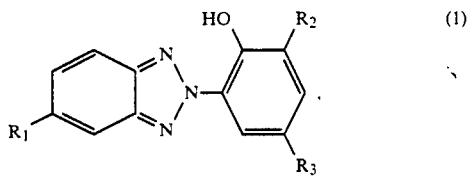

in which $R_1$ is hydrogen or chlorine and one of $R_2$ and $R_3$ is chlorine or lower alkyl and the other is a radical of the formula

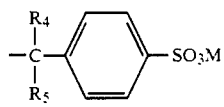

in which $R_4$ and $R_5$ independently of one another are hydrogen or methyl and M is hydrogen, an alkali metal or ammonium.

In the definition of $R_2$ and $R_3$ lower alkyl is a group containing 1 to 5, in particular 1 to 4, carbon atoms. Examples of groups of this type are methyl, ethyl, n-propyl, isopropyl, n-butyl, sec-butyl, tert-butyl, amyl, isoamyl or tert-amyl.

M is particularly potassium or sodium.

Compounds of particular interest are those in which $R_2$ is lower alkyl and $R_3$ is a radical of the formula (2), or those in which $R_2$ is a radical of the formula (2) and $R_3$ is lower alkyl.

The compounds of the formula (1) are prepared by sulfonating by means of sulfuric acid a compound of the formula (3)

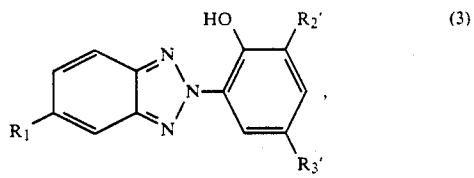

in which $R_1$ is as defined in formula (1) and one of $R_2'$ and $R_3'$ is chlorine or lower alkyl and the other is a radical of the formula (4)

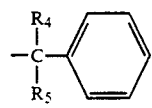

in which $R_4$ and $R_5$ are as defined in formula (2).

The sulfuric acid required for the sulfonation can be used in the form of concentrated sulfuric acid, sulfuric acid monohydrate or oleum of varying $SO_3$ content.

The reaction temperatures can vary between 0° and 30° C. If sulfuric acid monohydrate is used, temperatures from 0° to 30° C., in particular 20° to 25° C., are preferred. If, on the other hand, 5% oleum is used, temperatures from 0° to 30° C., in particular 15° to 25° C., are indicated.

Uniform monosulfonated 2-(2'-hydroxyphenyl)-benzotriazoles of the formula (1) can be prepared in a simple manner by means of the process according to the invention.

Monosulfonated 2-(2'-hydroxyphenyl)-benzotriazoles of the formula (1) are used as UV absorbers for polyamide fibres, wool and mixtures thereof. They can also be employed for preventing the yellowing of substrates, for example polyamide fibres, which have been treated with anti-stain agents, for example syntans.

The UV absorbers according to the invention can also be employed together with other stabilizers.

The following examples serve to illustrate the invention. The temperatures are quoted in °C.

PREPARATION EXAMPLES

EXAMPLE 1

12.7 g of 2-(2'-hydroxy-3'-methyl-5'-α,α-dimethylbenzylphenyl)-benzotriazole (melting point: 155°-156°) are introduced at room temperature into 120 g of 5% oleum in the course of 20 minutes and the mixture is stirred for a further 40 minutes at 20°-25°. The yellow solution is then stirred into 350 ml of 10% NaCl solution, in the course of which the temperature rises to approximately 75°. The precipitated acid is filtered off at room temperature and is then suspended in 200 ml of water and the pH of the suspension is adjusted to a value of 7 with 30% sodium hydroxide solution. The product is filtered off, washed with 10% NaCl solution and then with a 7:3 acetone/water mixture and dried in vacuo at 80°. This gives 13.8 g of a colourless product of the formula

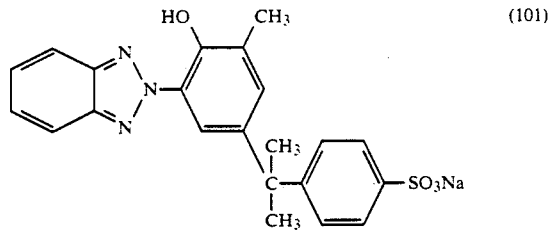

The procedure is repeated using 15.5 g of 2-(2'-hydroxy-3'-α,α-dimethylbenzylphenyl-5'-methylphenyl)-benzotriazole (melting point: 171°-173°) instead of 12.7 g of 2-(2'-hydroxy-3'-methyl-5'-α,α-dimethylbenzylphenyl)-benzotriazole, the procedure being otherwise the same. This gives 16.5 g of the product of the formula

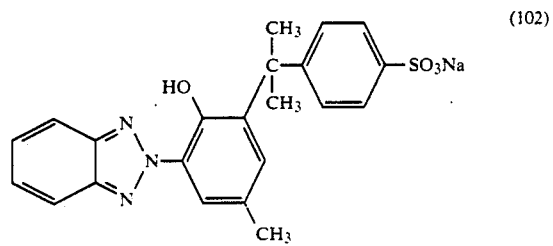

EXAMPLE 2

18 g of 2-(2'-hydroxy-3'α-phenylethyl-5'-methylphenyl)-benzotriazole (melting point 120°) are brought into 180 g of sulfuric acid monohydrate in the course of 10 minutes, with good stirring. The temperature should not exceed 25°. The yellow solution is then stirred at 23°-26° for one hour. After this the solution is stirred into 400 ml of a 5% NaCl solution in the course of approximately 5 minutes, the temperature rising to approximately 75°. After 10 g of NaCl have been added, the mixture is allowed to cool to room temperature and the precipitated product is filtered off and brought into 400 ml of water. The pH of the acid is adjusted to 7 with 30% sodium hydroxide solution. The mixture is then heated to 80°, in the course of which a solution is formed. After 20 g of NaCl have been added, the mixture is allowed to cool to room temperature and the precipitated product is filtered off, washed first with 2% NaCl solution and then with a 7:3 methanol/water mixture and is subsequently dried in vacuo at 80°.

This gives 21.5 g of the product of the formula

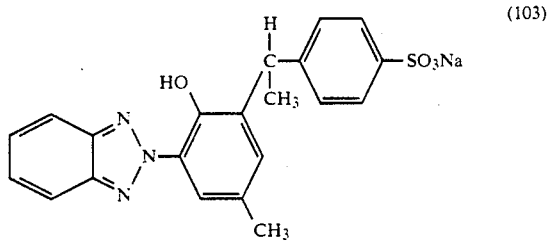

(103)

APPLICATION EXAMPLES

EXAMPLE 3

Four samples each of 10 g of a woollen serge fabric are "dyed blank" (with no dye) in 2 liquors and are dyed in two liquors in an open dyeing machine, for example an ®Ahiba, at a liquor ratio of 1:30. 4 identical liquors having the following additives are first prepared:

1.5 g/l of crystalline sodium acetate
2.0% of 80% acetic acid
5.0% of calcined sodium sulfate decahydrate and
1.0% of a levelling agent.

The woollen samples are treated in these liquors, warmed to 40°, for 10 minutes, a pH of 4.5 being set up. The samples are taken out of the liquors and the following additives are added:
Liquor 1: (blank dyeing 1): no additive
Liquor 2: (blank dyeing 2): 1% of the compound of the formula (103)
Liquor 3: (dyeing 1): the following dyes in a dissolved form:
0.005% of the compound of the formula and 0.01% of the compound of the formula

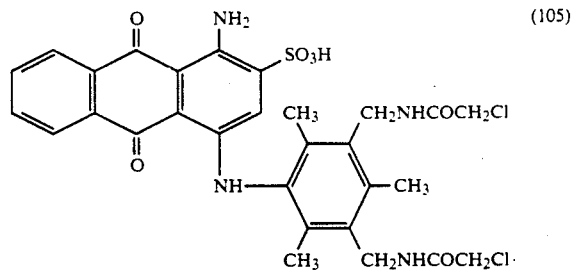

(105)

Liquor 4 (dyeing 2): This liquor contains 1% of the compound of the formula (103) and also 0.005% of the dye of the formula (104) and 0.01% of the dye of the formula (105).

The samples are put back into the dye liquor and are first treated for a further 10 minutes at 40° and are then heated to 90° at 1.5°/minute. The samples are treated at this temperature for 45 minutes, cooled to 60°, rinsed with cold water, centrifuged and dried at 70°. It can be seen from the table that the concomitant use of compound (103) results in lower yellowing of the wool and causes higher values of fastness to light in dyeings. The two blank dyeings and the untreated starting material are exposed to a xenon lamp as specified in DIN 75,202 for 72 hours and 144 hours (=1 and 2 test cycles, respectively) in an exposure apparatus. The yellowness value is then determined as specified in DIN 6167 from the colorimetric data. The light-fastness values of the two dyeings are determined as specified in SN-ISO 105-B02 (=xenon) and also as specified in DIN 75,202 (=Fakra). The results are shown in Table 1.

TABLE 1

| Treatment | Yellowness values 0/72/144 hours | Light-fastness values | |
|---|---|---|---|
| | | XENON | FAKRA |
| Blank dyeing 1 | 15.9/23.3/29.2 | — | — |
| Blank dyeing 2 | 17.0/19.9/24.3 | — | — |
| Dyeing 1 | — | 5 | 2 GH |
| Dyeing 2 | — | 6 | 3–4 GH |
| Starting material | 15.3/21.7/26.8 | — | — |

Assessment:
XENON against blue scale
FAKRA against grey scale

EXAMPLE 4

4 samples of a polyamide-6 woven tricot are treated in 4 liquors in an open dyeing machine, for example an ®AHIBA, at a liquor ratio of 1:30. All the liquors contain 1 g/l of ammonium sulfate and the following dyes (the percentages for the dyes relate to the weight of the fibre material):

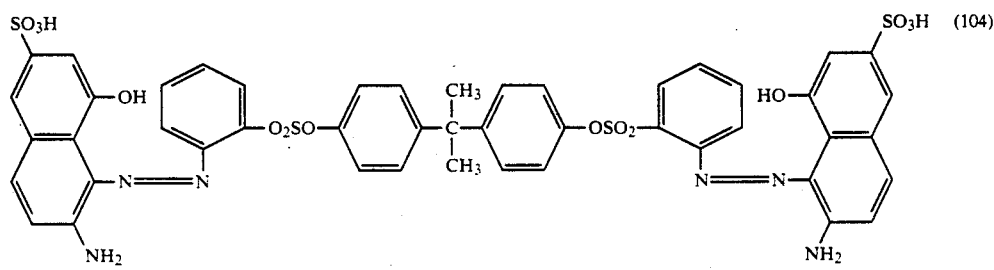

(104)

0.04% of the dye of the formula

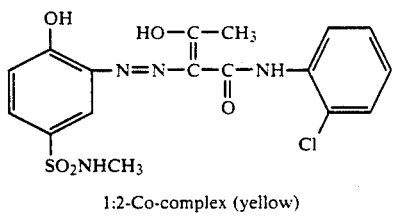

1:2-Co-complex (yellow)

0.025% of the dye of the formula

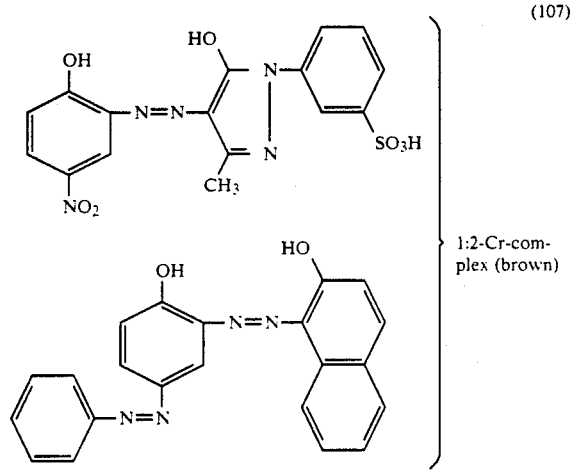

1:2-Cr-complex (brown)

and 0.003% of the dye of the formula

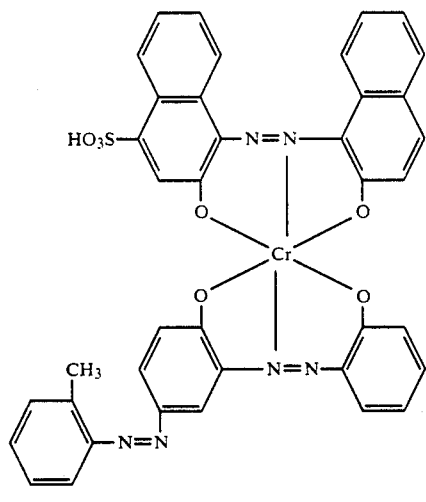

1:2-Cr-complex (black)

The following additives are added to the individual liquors:

Liquor 1: no further additives
Liquor 2: 0.5% of the compound of the formula (103)
Liquor 3: 0.03% of the compound of the formula

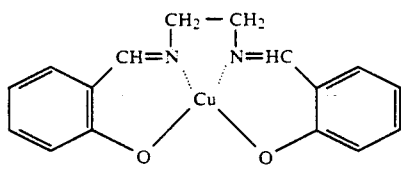

Liquor 4: 0.5% of the compound of the formula (103) and 0.03% of the compound of the formula (109).

The tricot samples are introduced at 40° into the dye liquors thus prepared, and are treated for about 5 minutes, heated to 95° at 1.5°/minute and treated at this temperature for a further 20 minutes, then 2% of 80% acetic acid is added and dyeing is carried out for a further 30 minutes. The samples are then cooled to 60°, rinsed with cold water, centrifuged and dried at 80° in a circulating air oven.

The light-fastness of the dyeings of the tricot samples is checked as specified in SN-ISO 105 B0.2 (=xenon) and DIN 75,202 (=Fakra). The results are collated in Table 2.

TABLE 2

| | Fastness to light | | | |
| | XENON | FAKRA 72 hours* | FAKRA 216 hours* | Note |
|---|---|---|---|---|
| Liquor 1 | 6 | 1 H | 1 H | The sample exposed for 216 hours as specified in Fakra is no longer resistant to tearing |
| Liquor 2 | 6–7 | 2 + GH | 1–2 + GH | — |
| Liquor 3 | 6 | 4 | 3–4 | — |
| Liquor 4 | 6–7 | 4–5 | 4 | — |

*Fakra 72 hours = one test cycle
*Fakra 216 hours = three test cycles

EXAMPLES 5 AND 6

Three 10 g samples of a woollen fabric (serge) are dyed as described in Example 1. However, 0.05% of the dye of the formula

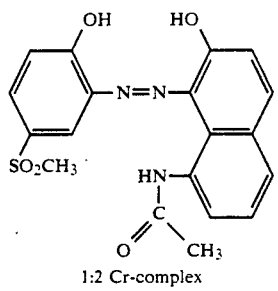

1:2 Cr-complex 0.08% of the dye of the formula (111)

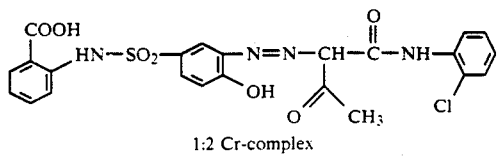

1:2 Cr-complex and 0.005% of the dye of the formula

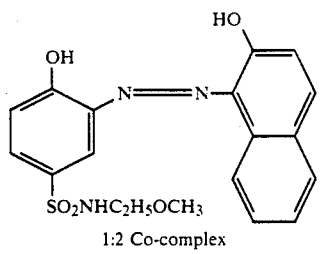

1:2 Co-complex and 0.75% of each of the compounds of the formulae (101) and (102) are employed, and a grey dyeing is produced.

The light-fastness of the dyeings is checked as specified in SN-ISO 105-BO2 (=XENON) and DIN 75,202 (FAKRA). Two-dimensional samples (13×4.5 cm) of the grey dyeings are also exposed for 144 hours to light as specified in DIN 75,202 and their tensile strength and elongation are checked as specified in Ser. No. 198,461. The results are shown in Table 3:

TABLE 3

| Dye-ing | Fastness to light | | | Tensile strength (%)/elongation* FAKRA after 144 hours | |
|---|---|---|---|---|---|
| | XENON | FAKRA 72 hours | FAKRA 144 hours | | |
| 1 | 5 | 2–3G | 1–2G | 38.1 | 27.5 |
| 2 | 5–6 | 3–4 | 2–3G | 45.2 | 35.8 |
| 3 | 5–6 | 4 | −3 | 46.1 | 37.1 |

*As specified in SN 198.461; relative to initial dyeings (=100%)

It can be seen that both the dyeing and the wool are stabilized by the compounds of the formulae (101) and (102), as a result of which their fastness to light and textile mechanical properties are improved.

What is claimed is:

1. A monosulfonated 2-(2'-hydroxyphenyl)-benzotriazole of the formula

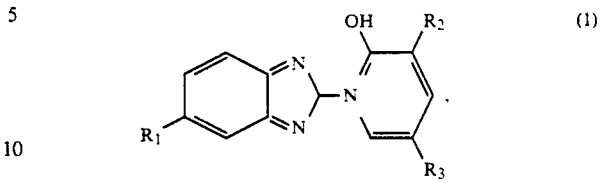

in which $R_1$ is hydrogen or chlorine and one of $R_2$ and $R_3$ is chlorine, methyl or ethyl and the other is a radical of the formula

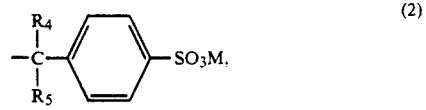

in which $R_4$ and $R_5$ independently of one another are hydrogen or methyl and M is hydrogen, potassium or sodium.

2. A monosulfonated 2-(2'-hydroxyphenyl)-benzotriazole according to claim 1, in which $R_2$ is methyl or ethyl and $R_3$ is a radical of the formula (2).

3. A monosulfonated 2-(2'-hydroxyphenyl)-benzotriazole according to claim 1, in which $R_2$ is a radical of the formula (2) and $R_3$ is methyl or ethyl.

4. A compound of claim 2 wherein $R_1$ is hydrogen and $R_2$, $R_4$ and $R_5$ are methyl.

5. A compound of claim 3 wherein $R_1$ and $R_4$ are hydrogen and $R_3$ and $R_5$ are methyl.

* * * * *